US00PP19789P2

(12) United States Plant Patent
Barrett

(10) Patent No.: US PP19,789 P2
(45) Date of Patent: Mar. 3, 2009

(54) WAX MYRTLE PLANT NAMED 'BTC-1'

(50) Latin Name: *Myrica cerifera*
Varietal Denomination: BTC-1

(76) Inventor: George Barnes Barrett, 3116 Applegate La., Augusta, GA (US) 30909

( * ) Notice: Subject to any disclaimer, the term of this patent is extended or adjusted under 35 U.S.C. 154(b) by 116 days.

(21) Appl. No.: 11/731,877

(22) Filed: Mar. 30, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of Wax Myrtle plant named 'BTC-1', characterized by its compact, upright and globular plant habit; short internodes and very freely branching habit; dense and bushy plant form; and dark green-colored foliage.

2 Drawing Sheets

Botanical designation: *Myrica cerifera.*
Cultivar denomination: 'BTC-1'.

BACKGROUND OF THE INVENTION

The present invention relates to a new and distinct cultivar of Wax Myrtle, botanically known as *Myrica cerifera,* and hereinafter referred to by the name 'BTC-1'.

The new Wax Myrtle originated from an open-pollination in 1996 in Augusta, Ga., of two unnamed selections of *Myrica cerifera,* not patented. The new Wax Myrtle was discovered and selected by the Inventor as a single flowering plant within the progeny of the stated open-pollination in a controlled environment in Augusta, Ga. in 1999.

Asexual reproduction of the new Wax Myrtle by cuttings in a controlled environment in Augusta, Ga. since 2000 has shown that the unique features of this new Wax Myrtle are stable and reproduced true to type in successive generations.

SUMMARY OF THE INVENTION

The cultivar BTC-1 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'BTC-1'. These characteristics in combination distinguish 'BTC-1' as a new and distinct cultivar of Wax Myrtle:

1. Compact, upright and globular plant habit.
2. Short internodes and very freely branching habit; dense and bushy plant form.
3. Dark green-colored foliage.

Plants of the new Wax Myrtle can be compared to plants of the parent selections. Plants of the new Wax Myrtle differ from plants of the parent selections in the following characteristics:

1. Plants of the new Wax Myrtle are more compact than plants of the parent selections.
2. Plants of the new Wax Myrtle are much more freely branching and have shorter internodes than plants of the parent selections. Consequentially, plants of the new Wax Myrtle are bushier and denser than and not as open and leggy as plants of the parent selections.
3. Leaves of plants of the new Wax Myrtle are darker green in color than leaves of plants of the parent selections.

Plants of the new Wax Myrtle can be compared to plants of the Wax Myrtle cultivar Emperor, not patented. In side-by-side comparisons conducted in Augusta, Ga., plants of the new Wax Myrtle differed from plants of the cultivar Emperor in the following characteristics:

1. Plants of the new Wax Myrtle were more compact than plants of the cultivar Emperor.
2. Plants of the new Wax Myrtle were much more freely branching than plants of the cultivar Emperor. Consequentially, plants of the new Wax Myrtle were bushier and denser than and not as open and leggy as plants of the cultivar Emperor.
3. Leaves of plants of the new Wax Myrtle were darker green in color than leaves of plants of the cultivar Emperor.

BRIEF DESCRIPTION OF THE PHOTOGRAPHS

The accompanying colored photographs illustrate the overall appearance of the new Wax Myrtle, showing the colors as true as it is reasonably possible to obtain in colored reproductions of this type. Colors in the photographs may differ slightly from the color values cited in the detailed botanical description which accurately describe the colors of the new Wax Myrtle.

The photograph on the first sheet comprises a side perspective view of a typical plant of 'BTC-1' grown in a container.

The photograph on the second sheet is a top perspective view of a typical plant of 'BTC-1'.

DETAILED BOTANICAL DESCRIPTION

The aforementioned photographs and following observations, measurements and values describe plants grown in Augusta, Ga. in an outdoor nursery during the winter and under conditions which closely approximate commercial production. Plants used for the photographs and for the detailed were about two years old. In the description, color references are made to The Royal Horticultural Society Colour Chart, 1995 Edition, except where general terms of ordinary dictionary significance are used.

Botanical classification: *Myrica cerifera* cultivar BTC-1.

Parentage:

*Female, or seed, parent.*—Unnamed selection of *Myrica cerifera,* not patented.

*Male, or pollen, parent.*—Unnamed selection of *Myrica cerifera,* not patented.

Propagation:

*Type.*—By cuttings.

*Time to initiate roots.*—About four to six weeks at 22° C. to 38° C.

*Root description.*—Fibrous; white in color, root apices, pink in color.

*Rooting habit.*—Freely branching; moderately dense.

Plant description:

*Plant habit.*—Perennial shrub. Compact, upright and globular plant habit. Short internodes and very freely branching habit; lateral branches potentially forming at every node; dense and bushy plant form. Vigorous growth habit.

*Plant height.*—About 65 cm.

*Plant diameter.*—About 67 cm.

Lateral branch description:

*Length.*—About 16.5 cm.

*Diameter.*—About 3 mm.

*Internode length.*—Relatively short, about 1 cm.

*Texture, young.*—Smooth, glabrous.

*Texture, older.*—Woody.

*Color, young.*—144A.

*Color, older.*—Close to 197A.

Foliage description:

*Arrangement.*—Alternate, simple.

*Length.*—About 4.75 cm.

*Width.*—About 1.4 cm.

*Shape.*—Lanceolate.

*Apex.*—Sharply acute.

*Base.*—Attenuate.

*Margin.*—Serrate; serrations widely-spaced.

*Fragrance.*—Moderate; typical of species.

*Texture, upper and lower surfaces.*—Smooth, glabrous; leathery.

*Luster, upper surface.*—Glossy.

*Luster, lower surface.*—Dull.

*Venation pattern.*—Pinnate.

*Color.*—Developing foliage, upper and lower surfaces: 144A. Fully expanded foliage, upper surface: Darker green than 147A; midvein, close to 147B; lateral veins, close to 147A, Fully expanded foliage, lower surface: More green than 147B; venation, close to 146A.

Flower description: Flower development has not been observed on plants of the new Wax Myrtle.

Garden performance: Plants of the new Wax Myrtle have been observed to tolerate wind, rain and temperatures ranging from about 1° C. to about 38° C.

Pathogen/pest resistance: Plants of the new Wax Myrtle have not been observed to be resistant to pathogens and pests common to Wax Myrtles.

It is claimed:

1. A new and distinct Wax Myrtle plant named 'BTC-1' as illustrated and described.

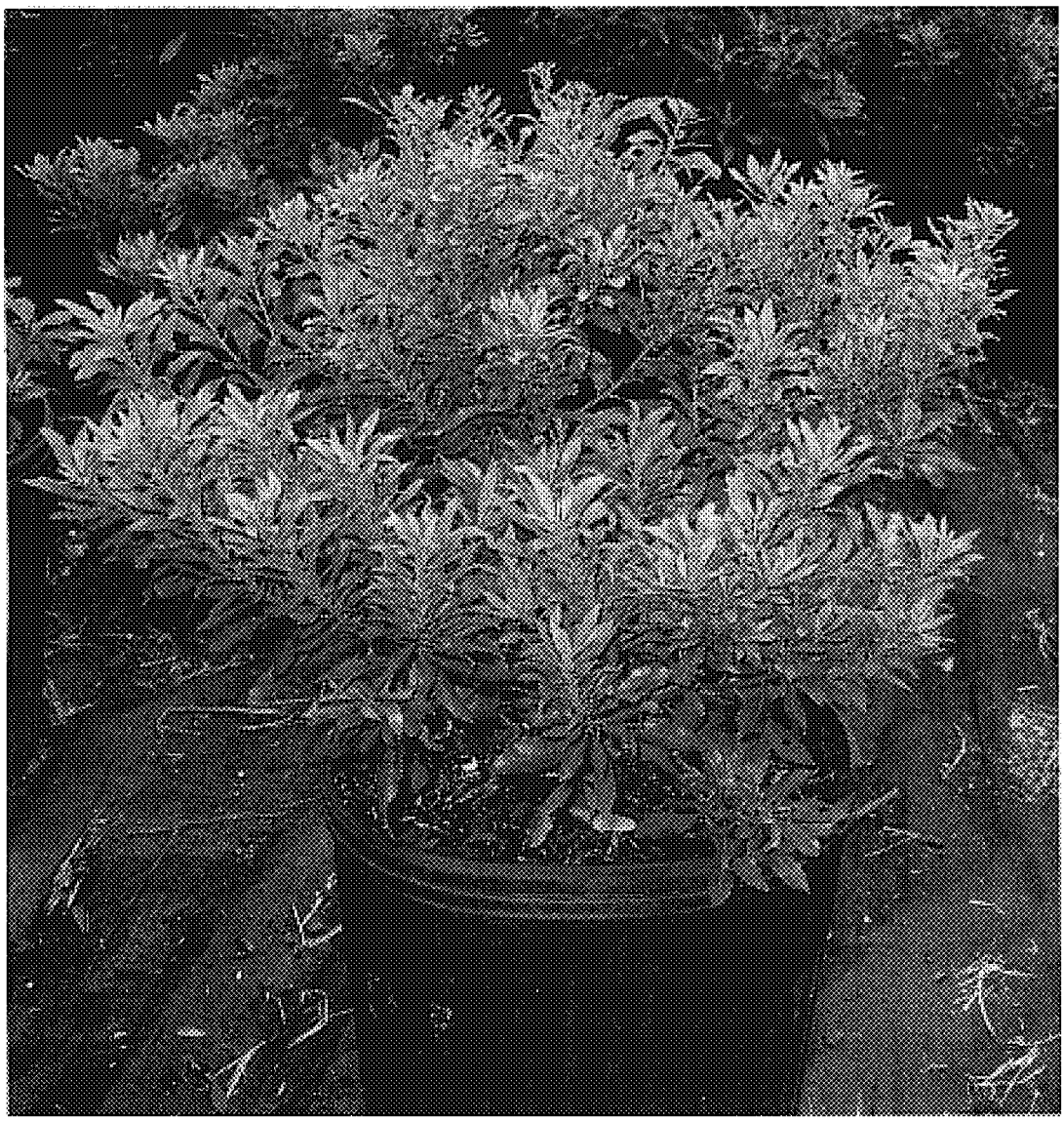

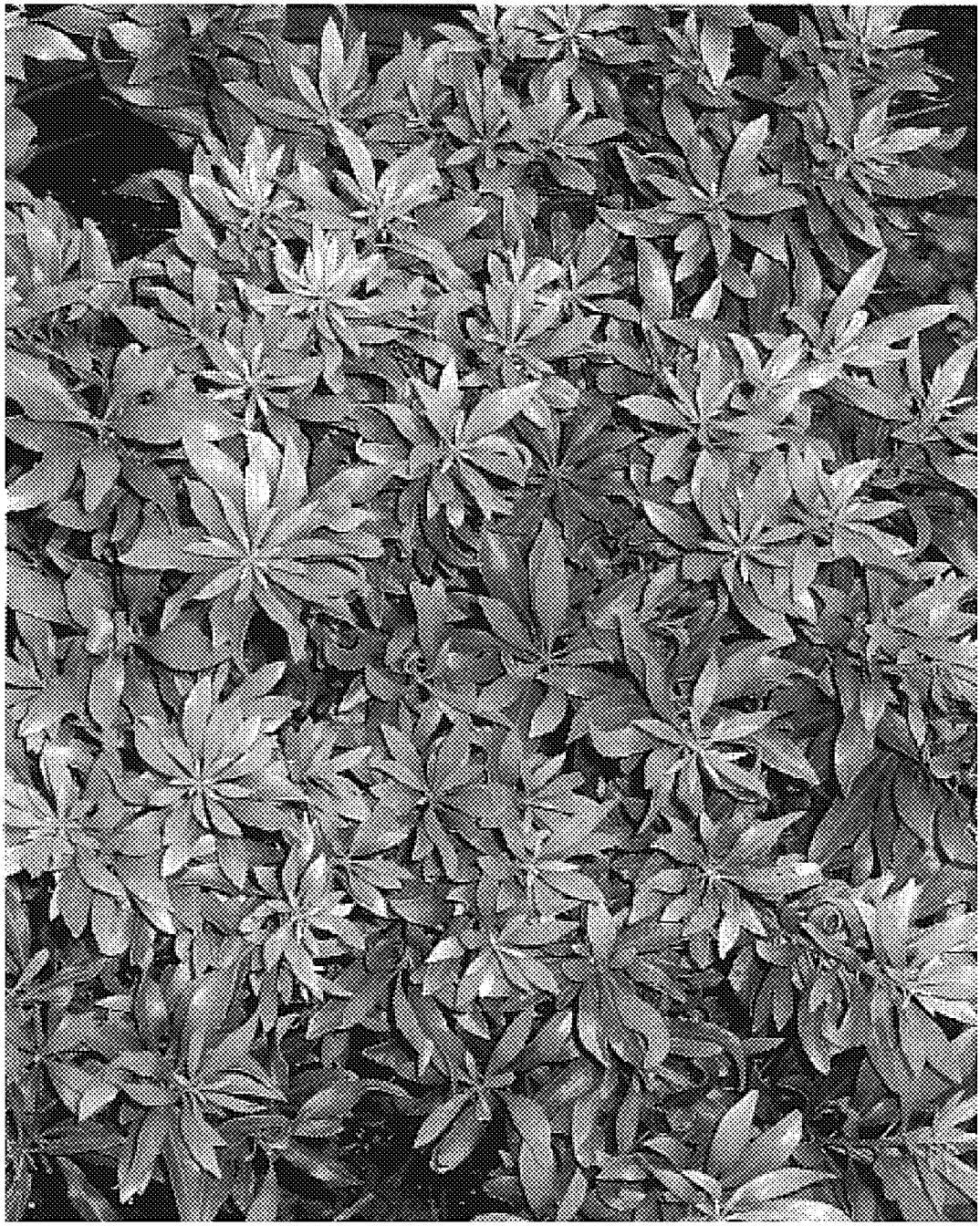

* * * * *